US012209492B2

(12) United States Patent
Jones et al.

(10) Patent No.: US 12,209,492 B2
(45) Date of Patent: Jan. 28, 2025

(54) RESERVOIR AND PRODUCTION SIMULATION USING ASPHALTENE ONSET PRESSURE MAP

(71) Applicant: Halliburton Energy Services, Inc., Houston, TX (US)

(72) Inventors: Christopher Michael Jones, Katy, TX (US); Rohin Naveena-Chandran, Houston, TX (US); Anthony Herman VanZuilekom, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 329 days.

(21) Appl. No.: 17/859,848

(22) Filed: Jul. 7, 2022

(65) Prior Publication Data

US 2023/0054254 A1 Feb. 23, 2023

Related U.S. Application Data

(60) Provisional application No. 63/234,049, filed on Aug. 17, 2021.

(51) Int. Cl.
*E21B 47/06* (2012.01)
*G01N 33/24* (2006.01)
(52) U.S. Cl.
CPC ............. *E21B 47/06* (2013.01); *G01N 33/24* (2013.01); *E21B 2200/20* (2020.05)
(58) Field of Classification Search
None
See application file for complete search history.

(56) References Cited

U.S. PATENT DOCUMENTS

| | | |
|---|---|---|
| 2005/0194134 A1 | 9/2005 | McGregor et al. |
| 2009/0192768 A1 | 7/2009 | Zuo et al. |
| 2012/0232859 A1* | 9/2012 | Pomerantz ............. G01V 1/282 |
| | | 703/2 |
| 2013/0311099 A1 | 11/2013 | Eyuboglu et al. |
| 2015/0211357 A1* | 7/2015 | Chen ..................... E21B 49/088 |
| | | 73/152.27 |

(Continued)

FOREIGN PATENT DOCUMENTS

WO 2011-138700 11/2011

OTHER PUBLICATIONS

U.S. Appl. No. 63/169,417 dated Apr. 1, 2021.

(Continued)

*Primary Examiner* — Raymond L Nimox
(74) *Attorney, Agent, or Firm* — John Wustenberg; C. Tumey Law Group PLLC

(57) ABSTRACT

A method and system for disposing a fluid sampling tool into a wellbore, taking a plurality of fluid samples with the fluid sampling tool, identifying a plurality of asphaltene onset pressures (AOP) downhole based at the least on the plurality of fluid samples. The method may further comprise forming an AOP map from at least the plurality of AOPs, identifying a laboratory property from at least one of the plurality of fluid samples; and developing a relational model between at least one of the plurality of AOPs and the laboratory property. The system may include a fluid sampling tool with one or more probes for injecting the one or more probes into a wellbore and taking a plurality of fluid samples from the wellbore.

20 Claims, 9 Drawing Sheets

(56) References Cited

U.S. PATENT DOCUMENTS

| | | |
|---|---|---|
| 2015/0309003 A1 | 10/2015 | Sullivan et al. |
| 2017/0342828 A1 | 11/2017 | Dumont et al. |
| 2018/0003619 A1* | 1/2018 | Sieben ............... G01N 33/2835 |
| 2018/0371904 A1 | 12/2018 | Van Zuilekom et al. |
| 2019/0017377 A1 | 1/2019 | He et al. |
| 2020/0041689 A1 | 2/2020 | Kirkwood et al. |
| 2020/0284140 A1 | 9/2020 | Jones et al. |
| 2020/0378250 A1 | 12/2020 | Olapade et al. |
| 2020/0400017 A1 | 12/2020 | Olapade et al. |
| 2021/0047924 A1 | 2/2021 | Kallehbasti et al. |
| 2021/0088447 A1 | 3/2021 | Stark et al. |
| 2021/0110246 A1 | 4/2021 | Chen et al. |
| 2021/0123313 A1 | 4/2021 | Westacott et al. |
| 2021/0123344 A1 | 4/2021 | Westacott et al. |
| 2021/0131283 A1 | 5/2021 | Jones et al. |
| 2021/0131951 A1 | 5/2021 | Dai et al. |
| 2021/0215033 A1 | 7/2021 | Jones et al. |
| 2021/0231001 A1 | 7/2021 | Jones et al. |
| 2021/0238999 A1 | 8/2021 | Naveena-Chandran et al. |
| 2021/0239000 A1 | 8/2021 | Olapade et al. |
| 2022/0074302 A1 | 3/2022 | Van Zuilekom et al. |

OTHER PUBLICATIONS

U.S. Appl. No. 63/234,050 dated Aug. 17, 2021.
International Search Report and Written Opinion for Application No. PCT/US2022/037547, dated Nov. 3, 2022.

* cited by examiner $P > P_{UAOP}$ $P = P_{UAOP}$
$P < P_{ARFO}$ $P = P_{ARFO}$
$P < P_{BP}$ $P = P_{BP}$
$P < P_{LAOP}$ $P_{BP} < P < P_{LOAP}$

RESERVOIR AND PRODUCTION SIMULATION USING ASPHALTENE ONSET PRESSURE MAP

BACKGROUND

Wells may be drilled at various depths to access and produce oil, gas, minerals, and other naturally-occurring deposits from subterranean geological formations. The drilling of a well is typically accomplished with a drill bit that is rotated within the well to advance the well by removing topsoil, sand, clay, limestone, calcites, dolomites, or other materials.

During or after drilling operations, sampling operations may be performed to collect a representative sample of formation or reservoir fluids (e.g., hydrocarbons) to further evaluate drilling operations and production potential, or to detect the presence of certain gases or other materials in the formation that may affect well performance.

The ability to reservoir fluid to flow freely to the surface is a constant challenge that affects the viability of an asset in all oil producing wellbore. The prevailing issue in the industry is asphaltenes. Asphaltenes are found in reservoir fluids and may fall out of solution due to a change in temperature or pressure as the reservoir fluid ascends to the surface. A proper understanding of asphaltene deposition lends itself to reliable completions planning, and timely remediation efforts. This ultimately dictates the production life of the reservoir.

Traditionally, identifying asphaltenes from a wellbore fluid is performed in a laboratory. Currently, technology is not able to identify asphaltenes from a wellbore fluid sample during downhole operations.

BRIEF DESCRIPTION OF THE DRAWINGS

The features and advantages of certain embodiments will be more readily appreciated when considered in conjunction with the accompanying figures. The figures are not to be construed as limiting any of the preferred embodiments.

DETAILED DESCRIPTION

The present disclosure relates to subterranean operations and, more particularly, embodiments disclosed herein provide methods and systems for identifying asphaltenes in a wellbore fluid sample downhole. This may allow for the construction of an asphaltene onset pressure (AOP) map. An AOP map may allow for and aid in determining reservoir simulation and production analysis and decisions with measurements performed downhole. Additionally, an AOP map produced with downhole measurements may be combined with Lab analysis AOP to interpolate AOP to positions not measured, and correlate with other physical or chemical properties of the fluid in order to provide production interpretation information and make production decisions.

The fluid sampling tools, systems and methods described herein may be used with any of the various techniques employed for evaluating a well, including without limitation wireline formation testing (WFT), measurement while drilling (MWD), and logging while drilling (LWD). The various tools and sampling units described herein may be delivered downhole as part of a wireline-delivered downhole assembly or as a part of a drill string. It should also be apparent that given the benefit of this disclosure, the apparatuses and methods described herein have applications in downhole operations other than drilling and may also be used after a well is completed.

Figure 1:
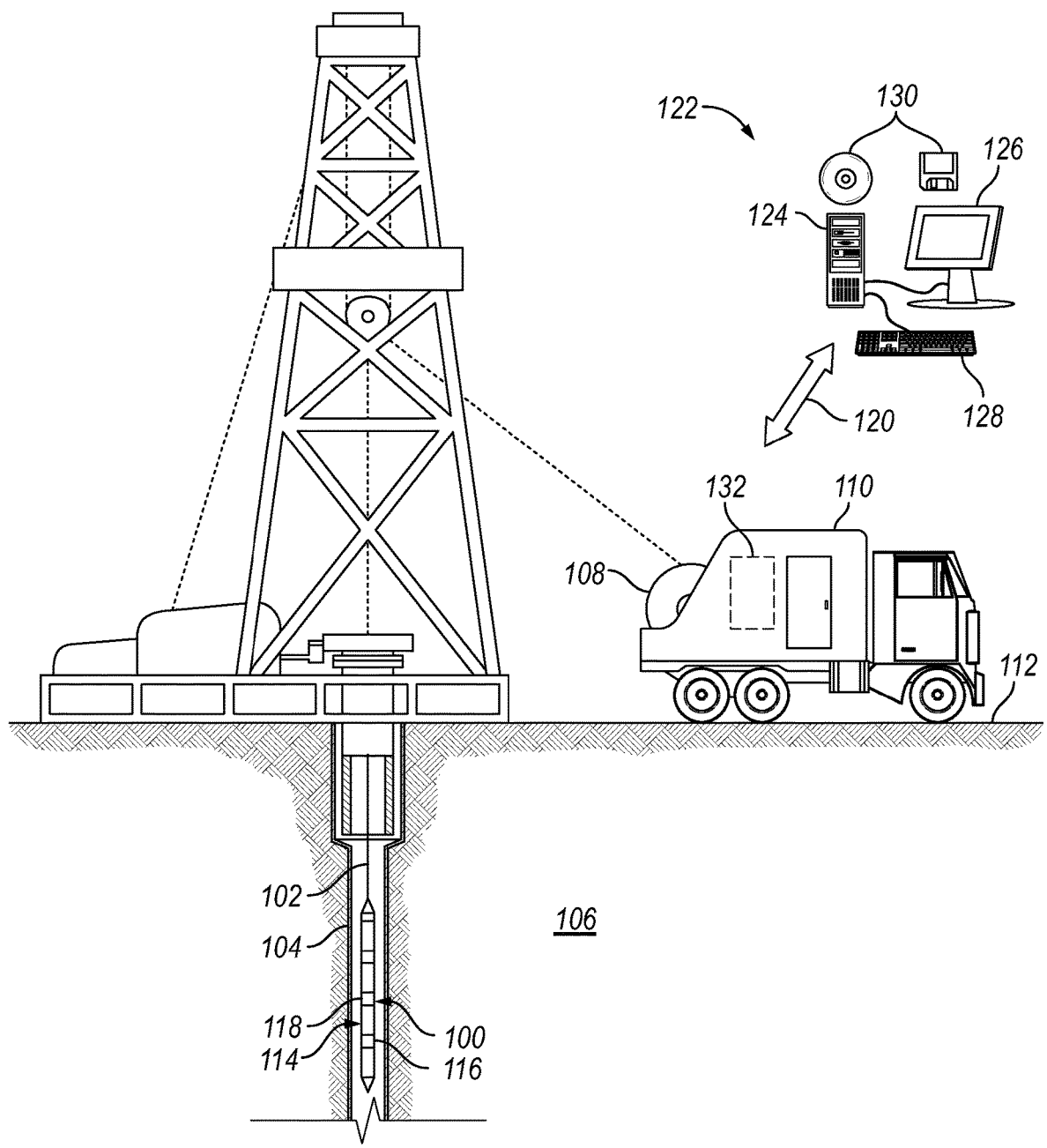
FIG. 1 illustrates a schematic view of a well in which an example embodiment of a fluid sample system is deployed.

FIG. 1 is a schematic diagram of downhole fluid sampling tool 100 on a conveyance 102. As illustrated, wellbore 104 may extend through subterranean formation 106. In examples, reservoir fluid may be contaminated with well fluid (e.g., drilling fluid) from wellbore 104. As described herein, the fluid sample may be analyzed to determine fluid contamination and other fluid properties of the reservoir fluid. As illustrated, a wellbore 104 may extend through subterranean formation 106. While the wellbore 104 is shown extending generally vertically into the subterranean formation 106, the principles described herein are also applicable to wellbores that extend at an angle through the subterranean formation 106, such as horizontal and slanted wellbores. For example, although FIG. 1 shows a vertical or low inclination angle well, high inclination angle or horizontal placement of the well and equipment is also possible. It should further be noted that while FIG. 1 generally depicts a land-based operation, those skilled in the art will readily recognize that the principles described herein are equally applicable to subsea operations that employ floating or sea-based platforms and rigs, without departing from the scope of the disclosure.

As illustrated, a hoist 108 may be used to run downhole fluid sampling tool 100 into wellbore 104. Hoist 108 may be disposed on a vehicle 110. Hoist 108 may be used, for example, to raise and lower conveyance 102 in wellbore 104. While hoist 108 is shown on vehicle 110, it should be understood that conveyance 102 may alternatively be disposed from a hoist 108 that is installed at surface 112 instead of being located on vehicle 110. Downhole fluid sampling tool 100 may be suspended in wellbore 104 on conveyance 102. Other conveyance types may be used for conveying downhole fluid sampling tool 100 into wellbore 104, including coiled tubing and wired drill pipe, for example. Downhole fluid sampling tool 100 may comprise a tool body 114, which may be elongated as shown on FIG. 1. Tool body 114 may be any suitable material, including without limitation titanium, stainless steel, alloys, plastic, combinations thereof, and the like. Downhole fluid sampling tool 100 may further include one or more sensors 116 for measuring properties of the fluid sample, reservoir fluid, wellbore 104, subterranean formation 106, or the like. In examples, downhole fluid sampling tool 100 may also include a fluid analysis module 118, which may be operable to process information regarding fluid sample, as described below. The downhole fluid sampling tool 100 may be used to collect fluid samples from subterranean formation 106 and may obtain and separately store different fluid samples from subterranean formation 106.

In examples, fluid analysis module 118 may comprise at least one a sensor that may continuously monitor a reservoir fluid. Such sensors include optical sensors, acoustic sensors, electromagnetic sensors, conductivity sensors, resistivity sensors, selective electrodes, density sensors, mass sensors, thermal sensors, chromatography sensors, viscosity sensors, bubble point sensors, fluid compressibility sensors, flow rate sensors, pressure sensors, and/or nuclear magnetic resonance (NMR) sensors, microfluidic sensor including but not limited to microfluidic pressure, volume, and temperature (PVT) phase behavior sensors. Sensors may measure a contrast between drilling fluid filtrate properties and formation fluid properties. Fluid analysis module 118 may be operable to derive properties and characterize the fluid sample. By way of example, fluid analysis module 118 may measure absorption, transmittance, or reflectance spectra and translate such measurements into component concentrations of the fluid sample, which may be lumped component concentrations, as described above. The fluid analysis module 118 may also measure gas-to-oil ratio, fluid composition, water cut, live fluid density, live fluid viscosity, formation pressure, and formation temperature. Fluid analysis module 118 may also be operable to determine fluid contamination of the fluid sample and may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. The absorption, transmittance, or reflectance spectra absorption, transmittance, or reflectance spectra may be measured with sensors 116 by way of standard operations. For example, fluid analysis module 118 may include random access memory (RAM), one or more processing units, such as a central processing unit (CPU), or hardware or software control logic, ROM, and/or other types of nonvolatile memory.

Any suitable technique may be used for transmitting signals from the downhole fluid sampling tool 100 to the surface 112. As illustrated, a communication link 120 (which may be wired or wireless, for example) may be provided that may transmit data from downhole fluid sampling tool 100 to an information handling system 122 at surface 112. Information handling system 122 may include a processing unit 124, a monitor 126, an input device 128 (e.g., keyboard, mouse, etc.), and/or computer media 130 (e.g., optical disks, magnetic disks) that can store code representative of the methods described herein. Information handling system 122 may act as a data acquisition system and possibly a data processing system that analyzes information from downhole fluid sampling tool 100. For example, information handling system 122 may process the information from downhole fluid sampling tool 100 for determination of fluid contamination. The information handling system 122 may also determine additional properties of the fluid sample (or reservoir fluid), such as component concentrations, pressure-volume-temperature properties (e.g., bubble point, phase envelop prediction, etc.) based on the fluid characterization. This processing may occur at surface 112 in real-time. Alternatively, the processing may occur downhole hole or at surface 112 or another location after recovery of downhole fluid sampling tool 100 from wellbore 104. Alternatively, the processing may be performed by an information handling system in wellbore 104, such as fluid analysis module 118. The resultant fluid contamination and fluid properties may then be transmitted to surface 112, for example, in real-time. Real time may be defined within any range comprising 0.01 seconds to 0.1 seconds, 0.1 seconds to 1 second, 1 second to 1 minute, 1 minute to 1 hour, 1 hour to 4 hours, or any combination of ranges provided.

Figure 2:
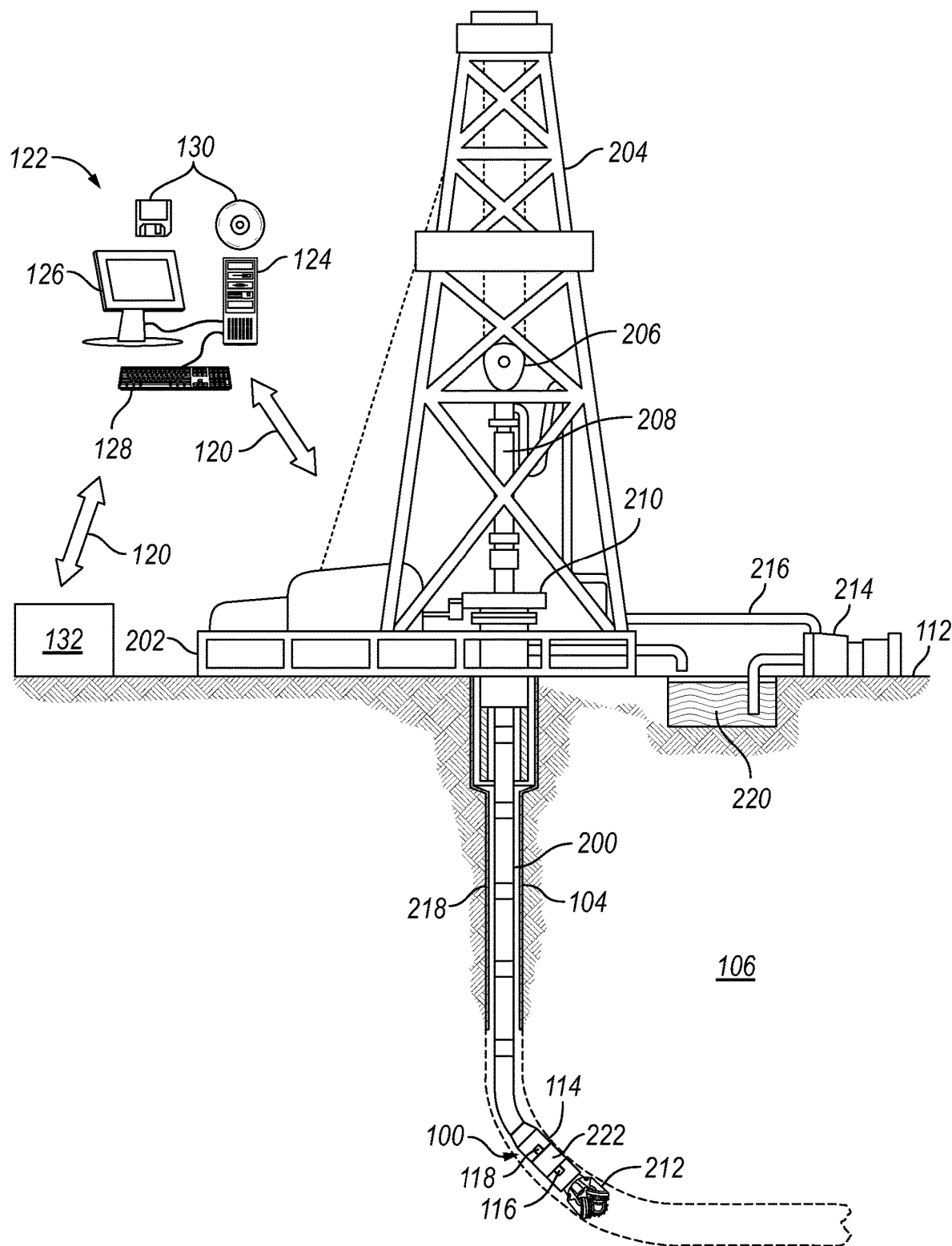
FIG. 2 illustrates a schematic view of another well in which an example embodiment of a fluid sample system is deployed.

Referring now to FIG. 2, a schematic diagram of downhole fluid sampling tool 100 disposed on a drill string 200 in a drilling operation. Downhole fluid sampling tool 100 may be used to obtain a fluid sample, for example, a fluid sample of a reservoir fluid from subterranean formation 106. The reservoir fluid may be contaminated with well fluid (e.g., drilling fluid) from wellbore 104. As described herein, the fluid sample may be analyzed to determine fluid contamination and other fluid properties of the reservoir fluid. As illustrated, a wellbore 104 may extend through subterranean formation 106. While the wellbore 104 is shown extending generally vertically into the subterranean formation 106, the principles described herein are also applicable to wellbores that extend at an angle through the subterranean formation 106, such as horizontal and slanted wellbores. For example, although FIG. 2 shows a vertical or low inclination angle well, high inclination angle or horizontal placement of the well and equipment is also possible. It should further be noted that while FIG. 2 generally depicts a land-based operation, those skilled in the art will readily recognize that the principles described herein are equally applicable to subsea operations that employ floating or sea-based platforms and rigs, without departing from the scope of the disclosure.

As illustrated, a drilling platform 202 may support a derrick 204 having a traveling block 206 for raising and lowering drill string 200. Drill string 200 may include, but is not limited to, drill pipe and coiled tubing, as generally known to those skilled in the art. A kelly 208 may support drill string 200 as it may be lowered through a rotary table 210. A drill bit 212 may be attached to the distal end of drill string 200 and may be driven either by a downhole motor and/or via rotation of drill string 200 from the surface 112. Without limitation, drill bit 212 may include, roller cone bits, PDC bits, natural diamond bits, any hole openers, reamers, coring bits, and the like. As drill bit 212 rotates, it may create and extend wellbore 104 that penetrates various subterranean formations 106. A pump 214 may circulate drilling fluid through a feed pipe 216 to kelly 208, downhole through interior of drill string 200, through orifices in drill bit 212, back to surface 112 via annulus 218 surrounding drill string 200, and into a retention pit 220.

Drill bit 212 may be just one piece of a downhole assembly that may include one or more drill collars 222 and downhole fluid sampling tool 100. Downhole fluid sampling tool 100, which may be built into the drill collars 222 may gather measurements and fluid samples as described herein. One or more of the drill collars 222 may form a tool body 114, which may be elongated as shown on FIG. 2. Tool body 114 may be any suitable material, including without limitation titanium, stainless steel, alloys, plastic, combinations thereof, and the like. Downhole fluid sampling tool 100 may be similar in configuration and operation to downhole fluid sampling tool 100 shown on FIG. 1 except that FIG. 2 shows downhole fluid sampling tool 100 disposed on drill string 200. Alternatively, the sampling tool may be lowered into the wellbore after drilling operations on a wireline.

Downhole fluid sampling tool 100 may further include one or more sensors 116 for measuring properties of the fluid sample reservoir fluid, wellbore 104, subterranean formation 106, or the like. The one or more sensors 116 may be disposed within fluid analysis module 118. In examples, more than one fluid analysis module may be disposed on drill string 200. The properties of the fluid are measured as the fluid passes from the formation through the tool and into either the wellbore or a sample container. As fluid is flushed in the near wellbore region by the mechanical pump, the fluid that passes through the tool generally reduces in drilling fluid filtrate content, and generally increases in formation fluid content. The downhole fluid sampling tool 100 may be used to collect a fluid sample from subterranean formation 106 when the filtrate content has been determined to be sufficiently low. Sufficiently low depends on the purpose of sampling. For some laboratory testing below 10% drilling fluid contamination is sufficiently low, and for other testing below 1% drilling fluid filtrate contamination is sufficiently low. Sufficiently low also depends on the nature of the formation fluid such that lower requirements are generally needed, the lighter the oil as designated with either a higher GOR or a higher API gravity. Sufficiently low also depends on the rate of cleanup in a cost benefit analysis since longer pumpout times required to incrementally reduce the contamination levels may have prohibitively large costs. As previously described, the fluid sample may comprise a reservoir fluid, which may be contaminated with a drilling fluid or drilling fluid filtrate. Downhole fluid sampling tool 100 may obtain and separately store different fluid samples from subterranean formation 106 with fluid analysis module 118. Fluid analysis module 118 may operate and function in the same manner as described above. However, storing of the fluid samples in the downhole fluid sampling tool 100 may be based on the determination of the fluid contamination. For example, if the fluid contamination exceeds a tolerance, then the fluid sample may not be stored. If the fluid contamination is within a tolerance, then the fluid sample may be stored in the downhole fluid sampling tool 100. In examples, contamination may be defined within fluid analysis module 118.

As previously described, information from downhole fluid sampling tool 100 may be transmitted to an information handling system 122, which may be located at surface 112. As illustrated, communication link 120 (which may be wired or wireless, for example) may be provided that may transmit data from downhole fluid sampling tool 100 to an information handling system 111 at surface 112. Information handling system 140 may include a processing unit 124, a monitor 126, an input device 128 (e.g., keyboard, mouse, etc.), and/or computer media 130 (e.g., optical disks, magnetic disks) that may store code representative of the methods described herein. In addition to, or in place of processing at surface 112, processing may occur downhole (e.g., fluid analysis module 118). In examples, information handling system 122 may perform computations to estimate asphaltenes within a fluid sample.

Figure 3:
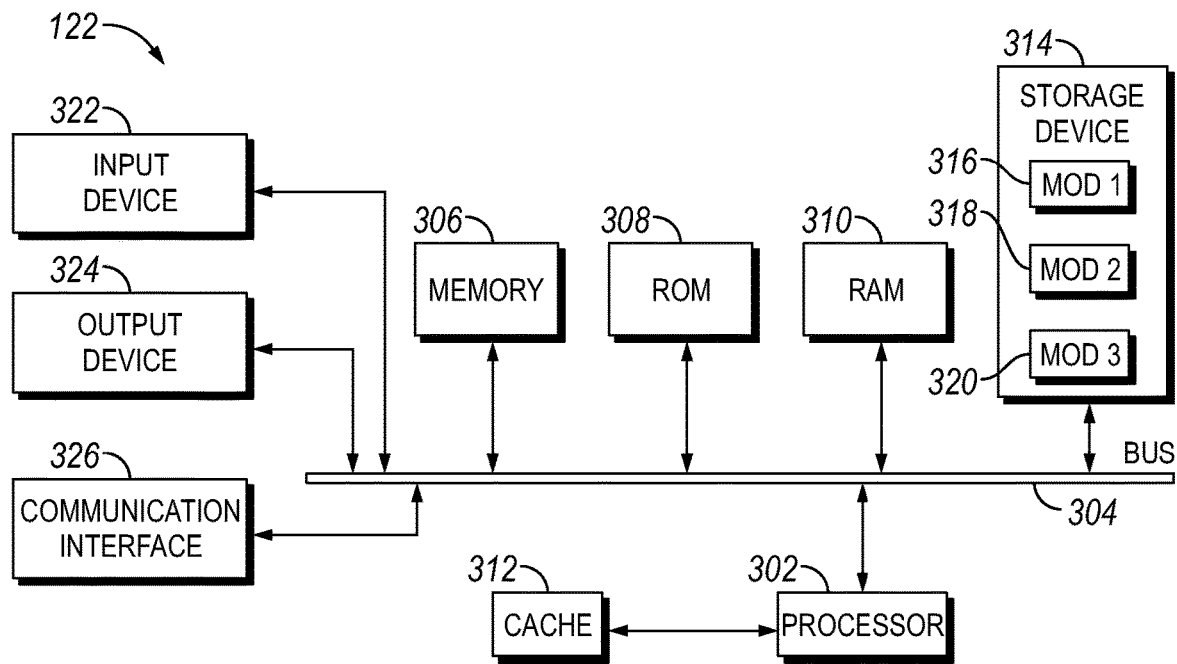
FIG. 3 illustrates a schematic view of a chipset in an information handling system.

FIG. 3 illustrates an example information handling system 138 which may be employed to perform various steps, methods, and techniques disclosed herein. Persons of ordinary skill in the art will readily appreciate that other system examples are possible. As illustrated, information handling system 138 includes a processing unit (CPU or processor) 302 and a system bus 304 that couples various system components including system memory 306 such as read only memory (ROM) 308 and random access memory (RAM) 310 to processor 302. Processors disclosed herein may all be forms of this processor 302. Information handling system 138 may include a cache 312 of high-speed memory connected directly with, in close proximity to, or integrated as part of processor 302. Information handling system 138 copies data from memory 306 and/or storage device 314 to cache 312 for quick access by processor 302. In this way, cache 312 provides a performance boost that avoids processor 302 delays while waiting for data. These and other modules may control or be configured to control processor 302 to perform various operations or actions. Other system memory 306 may be available for use as well. Memory 306 may include multiple different types of memory with different performance characteristics. It may be appreciated that the disclosure may operate on information handling system 138 with more than one processor 302 or on a group or cluster of computing devices networked together to provide greater processing capability. Processor 302 may include any general purpose processor and a hardware module or software module, such as first module 316, second module 318, and third module 320 stored in storage device 314, configured to control processor 302 as well as a special-purpose processor where software instructions are incorporated into processor 302. Processor 302 may be a self-contained computing system, containing multiple cores or processors, a bus, memory controller, cache, etc. A multi-core processor may be symmetric or asymmetric. Processor 302 may include multiple processors, such as a system having multiple, physically separate processors in different sockets, or a system having multiple processor cores on a single physical chip. Similarly, processor 302 may include multiple distributed processors located in multiple separate computing devices but working together such as via a communications network. Multiple processors or processor cores may share resources such as memory 306 or cache 312 or may operate using independent resources. Processor 302 may include one or more state machines, an application specific integrated circuit (ASIC), or a programmable gate array (PGA) including a field PGA (FPGA).

Each individual component discussed above may be coupled to system bus 304, which may connect each and every individual component to each other. System bus 304 may be any of several types of bus structures including a memory bus or memory controller, a peripheral bus, and a local bus using any of a variety of bus architectures. A basic input/output (BIOS) stored in ROM 308 or the like, may provide the basic routine that helps to transfer information between elements within information handling system 138, such as during start-up. Information handling system 138 further includes storage devices 314 or computer-readable storage media such as a hard disk drive, a magnetic disk drive, an optical disk drive, tape drive, solid-state drive, RAM drive, removable storage devices, a redundant array of inexpensive disks (RAID), hybrid storage device, or the like. Storage device 314 may include software modules 316, 318, and 320 for controlling processor 302. Information handling system 138 may include other hardware or software modules. Storage device 314 is connected to the system bus 304 by a drive interface. The drives and the associated computer-readable storage devices provide nonvolatile storage of computer-readable instructions, data structures, program modules and other data for information handling system 138. In one aspect, a hardware module that performs a particular function includes the software component stored in a tangible computer-readable storage device in connection with the necessary hardware components, such as processor 302, system bus 304, and so forth, to carry out a particular function. In another aspect, the system may use a processor and computer-readable storage device to store instructions which, when executed by the processor, cause the processor to perform operations, a method or other specific actions.

The basic components and appropriate variations may be modified depending on the type of device, such as whether information handling system 138 is a small, handheld computing device, a desktop computer, or a computer server. When processor 302 executes instructions to perform "operations", processor 302 may perform the operations directly and/or facilitate, direct, or cooperate with another device or component to perform the operations.

As illustrated, information handling system 138 employs storage device 314, which may be a hard disk or other types of computer-readable storage devices which may store data that are accessible by a computer, such as magnetic cassettes, flash memory cards, digital versatile disks (DVDs), cartridges, random access memories (RAMs) 310, read only memory (ROM) 308, a cable containing a bit stream and the like, may also be used in the exemplary operating environment. Tangible computer-readable storage media, computer-readable storage devices, or computer-readable memory devices, expressly exclude media such as transitory waves, energy, carrier signals, electromagnetic waves, and signals per se.

To enable user interaction with information handling system 138, an input device 322 represents any number of input mechanisms, such as a microphone for speech, a touch-sensitive screen for gesture or graphical input, keyboard, mouse, motion input, speech and so forth. Additionally, input device 322 may take in data from one or more sensors 136, discussed above. An output device 324 may also be one or more of a number of output mechanisms known to those of skill in the art. In some instances, multimodal systems enable a user to provide multiple types of input to communicate with information handling system 138. Communications interface 326 generally governs and manages the user input and system output. There is no restriction on operating on any particular hardware arrangement and therefore the basic hardware depicted may easily be substituted for improved hardware or firmware arrangements as they are developed.

As illustrated, each individual component describe above is depicted and disclosed as individual functional blocks. The functions these blocks represent may be provided through the use of either shared or dedicated hardware, including, but not limited to, hardware capable of executing software and hardware, such as a processor 302, that is purpose-built to operate as an equivalent to software executing on a general purpose processor. For example, the functions of one or more processors presented in FIG. 3 may be provided by a single shared processor or multiple processors. (Use of the term "processor" should not be construed to refer exclusively to hardware capable of executing software.) Illustrative embodiments may include microprocessor and/or digital signal processor (DSP) hardware, read-only memory (ROM) 308 for storing software performing the operations described below, and random-access memory (RAM) 310 for storing results. Very large-scale integration (VLSI) hardware embodiments, as well as custom VLSI circuitry in combination with a general-purpose DSP circuit, may also be provided.

The logical operations of the various methods, described below, are implemented as: (1) a sequence of computer implemented steps, operations, or procedures running on a programmable circuit within a general use computer, (2) a sequence of computer implemented steps, operations, or procedures running on a specific-use programmable circuit; and/or (3) interconnected machine modules or program engines within the programmable circuits. Information handling system 138 may practice all or part of the recited methods, may be a part of the recited systems, and/or may operate according to instructions in the recited tangible computer-readable storage devices. Such logical operations may be implemented as modules configured to control processor 302 to perform particular functions according to the programming of software modules 316, 318, and 320.

In examples, one or more parts of the example information handling system 138, up to and including the entire information handling system 138, may be virtualized. For example, a virtual processor may be a software object that executes according to a particular instruction set, even when a physical processor of the same type as the virtual processor is unavailable. A virtualization layer or a virtual "host" may enable virtualized components of one or more different computing devices or device types by translating virtualized operations to actual operations. Ultimately however, virtualized hardware of every type is implemented or executed by some underlying physical hardware. Thus, a virtualization compute layer may operate on top of a physical compute layer. The virtualization compute layer may include one or more virtual machines, an overlay network, a hypervisor, virtual switching, and any other virtualization application.

Figure 4:
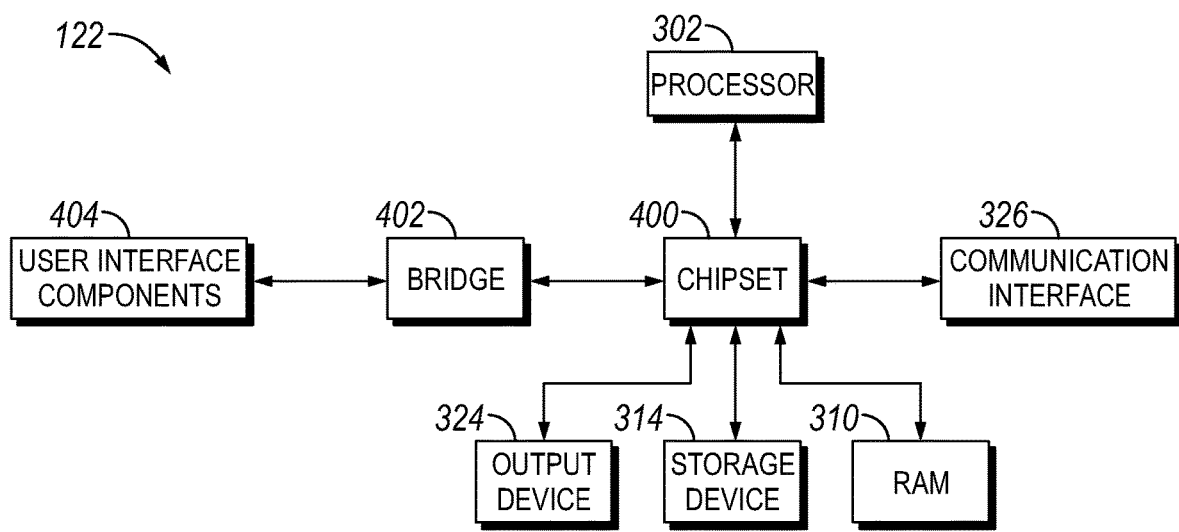
FIG. 4 illustrates the chipset in communication with other components of the information handling system.

FIG. 4 illustrates an example information handling system 138 having a chipset architecture that may be used in executing the described method and generating and displaying a graphical user interface (GUI). Information handling system 138 is an example of computer hardware, software, and firmware that may be used to implement the disclosed technology. Information handling system 138 may include a processor 302, representative of any number of physically and/or logically distinct resources capable of executing software, firmware, and hardware configured to perform identified computations. Processor 302 may communicate with a chipset 400 that may control input to and output from processor 302. In this example, chipset 400 outputs information to output device 324, such as a display, and may read and write information to storage device 314, which may include, for example, magnetic media, and solid-state media. Chipset 400 may also read data from and write data to RAM 310. A bridge 402 for interfacing with a variety of user interface components 404 may be provided for interfacing with chipset 400. Such user interface components 404 may include a keyboard, a microphone, touch detection and processing circuitry, a pointing device, such as a mouse, and so on. In general, inputs to information handling system 138 may come from any of a variety of sources, machine generated and/or human generated.

Chipset 400 may also interface with one or more communication interfaces 326 that may have different physical interfaces. Such communication interfaces may include interfaces for wired and wireless local area networks, for broadband wireless networks, as well as personal area networks. Some applications of the methods for generating, displaying, and using the GUI disclosed herein may include receiving ordered datasets over the physical interface or be generated by the machine itself by processor 302 analyzing data stored in storage device 314 or RAM 310. Further, information handling system 138 receive inputs from a user via user interface components 404 and execute appropriate functions, such as browsing functions by interpreting these inputs using processor 302.

In examples, information handling system 138 may also include tangible and/or non-transitory computer-readable storage devices for carrying or having computer-executable instructions or data structures stored thereon. Such tangible computer-readable storage devices may be any available device that may be accessed by a general purpose or special purpose computer, including the functional design of any special purpose processor as described above. By way of example, and not limitation, such tangible computer-readable devices may include RAM, ROM, EEPROM, CD-ROM or other optical disk storage, magnetic disk storage or other magnetic storage devices, or any other device which may be used to carry or store desired program code in the form of computer-executable instructions, data structures, or processor chip design. When information or instructions are provided via a network, or another communications connection (either hardwired, wireless, or combination thereof), to a computer, the computer properly views the connection as a computer-readable medium. Thus, any such connection is properly termed a computer-readable medium. Combinations of the above should also be included within the scope of the computer-readable storage devices.

Computer-executable instructions include, for example, instructions and data which cause a general-purpose computer, special purpose computer, or special purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

In additional examples, methods may be practiced in network computing environments with many types of computer system configurations, including personal computers, hand-held devices, multi-processor systems, microprocessor-based or programmable consumer electronics, network PCs, minicomputers, mainframe computers, and the like. Examples may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices. During drilling operations information handling system 138 may process different types of the real time data which may be utilized to create an asphaltene onset pressure map (AOP).

Figure 5:
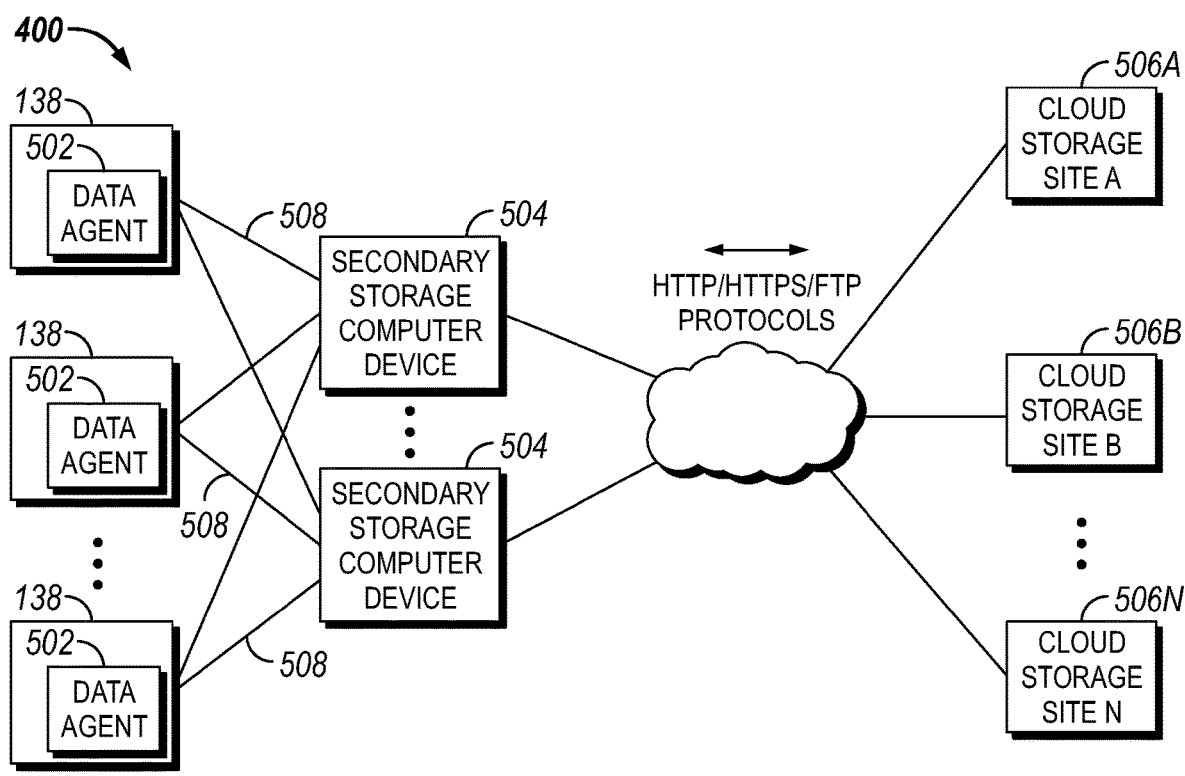
FIG. 5 illustrates a schematic view of a cloud based system.

FIG. 5 illustrates an example of one arrangement of resources in a computing network 500 that may employ the processes and techniques described herein, although many others are of course possible. As noted above, an information handling system 138, as part of their function, may utilize data, which includes files, directories, metadata (e.g., access control list (ACLS) creation/edit dates associated with the data, etc.), and other data objects. The data on the information handling system 138 is typically a primary copy (e.g., a production copy). During a copy, backup, archive or other storage operation, information handling system 138 may send a copy of some data objects (or some components thereof) to a secondary storage computing device 504 by utilizing one or more data agents 502.

A data agent 502 may be a desktop application, website application, or any software-based application that is run on information handling system 138. As illustrated, information handling system 138 may be disposed at any rig site (e.g., referring to FIG. 1) or repair and manufacturing center. Data agent 502 may communicate with a secondary storage computing device 504 using communication protocol 508 in a wired or wireless system. Communication protocol 508 may function and operate as an input to a website application. In the website application, field data related to pre- and post-operations, generated DTCs, notes, and the like may be uploaded. Additionally, information handling system 138 may utilize communication protocol 508 to access processed measurements, operations with similar DTCs, troubleshooting findings, historical run data, and/or the like. This information is accessed from secondary storage computing device 504 by data agent 502, which is loaded on information handling system 138.

Secondary storage computing device 504 may operate and function to create secondary copies of primary data objects (or some components thereof) in various cloud storage sites 506A-N. Additionally, secondary storage computing device 504 may run determinative algorithms on data uploaded from one or more information handling systems 138, discussed further below. Communications between the secondary storage computing devices 504 and cloud storage sites 506A-N may utilize REST protocols (Representational state transfer interfaces) that satisfy basic C/R/U/D semantics (Create/Read/Update/Delete semantics), or other hypertext transfer protocol ("HTTP")-based or file-transfer protocol ("FTP")-based protocols (e.g., Simple Object Access Protocol).

In conjunction with creating secondary copies in cloud storage sites 506A-N, the secondary storage computing device 504 may also perform local content indexing and/or local object-level, sub-object-level or block-level deduplication when performing storage operations involving various cloud storage sites 506A-N. Cloud storage sites 506A-N may further record and maintain DTC code logs for each downhole operation or run, map DTC codes, store repair and maintenance data, store operational data, and/or provide outputs from determinative algorithms that are fun at cloud storage sites 506A-N. This type of network may be utilized to an asphaltene onset pressure map (AOP).

As such, input layer 604 may include any number of inputs 608. Inputs 608 may comprise properties of fluid and/or fluid formations such as physical properties (bulk or molecular) such as density, index of refraction, compressibility, bubble point, phase and/or other phase behavior properties measured by sampling tool 100. In examples, inputs may also include transport properties such as viscosity or thermal conductivity. Fluid analysis modules 118 may determine optical, chromatographic, mass spectrometry, density sensor, viscosity sensor, phase change apparatus compressibility sensor resistivity sensor, capacitance or dielectric sensor acoustic sensor, or combinations therein. Additionally, inputs 608 may also include chemical properties including composition i.e., hydrocarbon composition (methane, ethane propane, butane, pentane, hexane, higher hydrocarbons) and or chemical classes such as but not limited to Saturates, Aromatics, Resins or Asphaltenes chemical classes, and their respective concentrations of the various components, pH, eH, chemical potential, reactivity, fluid compatibility, and/or scaling potential. Fluid analysis modules 118 may determine optical, chromatographic, mass spectrometry, density sensor, viscosity sensor, phase change apparatus compressibility sensor resistivity sensor, capacitance or dielectric sensor acoustic sensor, or combinations therein. In other examples, inputs may include raw sensor measurements such as temperature, pressure, optical information, acoustic information, and/or electromagnetic information. Fluid analysis modules 118 may determine optical, chromatographic, mass spectrometry, density sensor, viscosity sensor, phase change apparatus compressibility sensor resistivity sensor, capacitance or dielectric sensor acoustic sensor, or combinations therein. In examples, output layer 606 may form outputs 606. Outputs 610 may comprise other unmeasured or less well measured physical or chemical properties, and/or correlated sensor measurements. For instance, outputs 610 may comprise scaling potential, or asphaltene onset pressure if not directly measured. Alternatively, the model may provide outputs 610 for enhanced resolution, precision or accuracy refinement of a measured property such as bubble point, or asphaltene onset pressure which may be included as an input 608 but refined as an enhanced measurement as an output 610 in output layer 606. Any of the inputs 608 or outputs 610 may be from the current well being evaluated or analogue wells which may be in the field, in the basis, or not so if other characteristics such as but not limited to formation type or formation fluid provide a basis for analogy. During operations, inputs 608 data are given to neurons 612 in input layer 604. Neurons 612, 614, and 616 are defined as individual or multiple information handling systems 122 connected in a network, which may compute information to make drilling, completion or production decisions such as but not limited how to drill the well, where to drill the well, how to complete a well, or where to complete a well, or how to produce a well, or where to produce a well. Any of computations may be from the current well being evaluated or analogue wells which may be in the field, in the basis, or not so if other characteristics such as but not limited to formation type or formation fluid provide a basis for analogy. The output from neurons 612 may be transferred to one or more neurons 614 within one or more hidden layers 602. Hidden layers 602 includes one or more neurons 614 connected in a network that further process information from neurons 612. The number of hidden layers 602 and neurons 612 in hidden layer 602 may be determined by personnel that designs NN 600. Hidden layers 602 is defined as a set of information handling system 122 assigned to specific processing. Hidden layers 602 spread computation to multiple neurons 606, which may allow for faster computing, processing, training, and learning by NN 600. Output layers 606 may combine the processing in hidden layers 602, using neurons 616, to form an asphaltene onset pressure (AOP). By any of the modeling methods, output layers 606, wherein other methods may use different layer or subfunction structuring, may be coordinated such that simultaneously an AOP may be provided for different outputs each corresponding to a different depths or lateral distance across a field or distance from an injecting well, temperature or other state condition comprising at least formation or concentration of materials. Multiple outputs may be coordinated wherein the multiple outputs are different but related parameters which may include but is not limited to asphaltene onset pressure, and asphaltene stability index, either static for a single state, or as a function independent variable such as but not limited to depth or lateral distance across a field or distance from an injecting well or of state variables such as but not limited to temperature. Other modeling methods include equations of state, kriging methods, random forest methods, classification methods, multivariate analysis methods and combinations therein.

Figure 7:
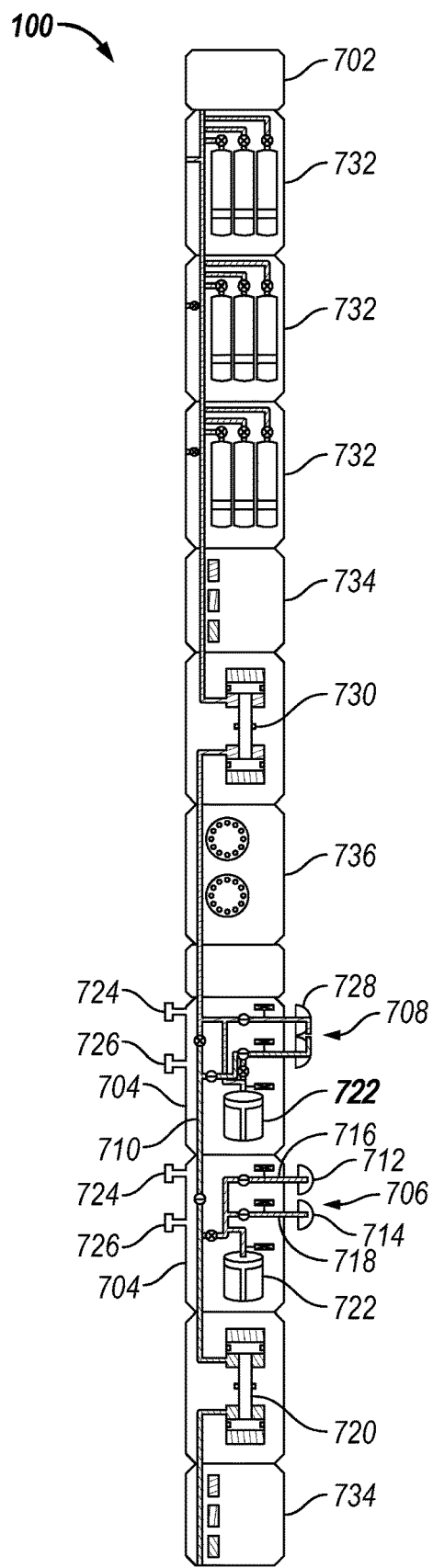
FIG. 7 illustrates a schematic view of an example embodiment of a fluid sampling tool.

FIG. 7 illustrates a schematic of fluid sampling tool 100. As illustrated, fluid sampling tool 100 includes a power telemetry section 702 through which fluid sampling tool 100 may communicate with other actuators and sensors in a conveyance (e.g., conveyance 102 on FIG. 1 or drill string 200 on FIG. 2), the conveyance's communications system, such as information handling system 138 (e.g., referring to FIG. 1). In examples, power telemetry section 702 may also be a port through which the various actuators (e.g., valves) and sensors (e.g., temperature and pressure sensors) in fluid sampling tool 100 may be controlled and monitored. In examples, power telemetry section 702 includes an information handling system that exercises the control and monitoring function. In one example, the control and monitoring function is performed by an information handling system in another part of the drill string or wireline tool (not shown) or by an information handling system at surface 112.

Information from fluid sampling tool 100 may be gathered and/or processed by the information handling system 138 (e.g., referring to FIGS. 1 and 2). The processing may be performed real-time during data acquisition or after recovery of fluid sampling tool 100. Processing may alternatively occur downhole or may occur both downhole and at surface. In some examples, signals recorded by fluid sampling tool 100 may be conducted to information handling system by way of conveyance. Information handling system may process the signals, and the information contained therein may be displayed for an operator to observe and stored for future processing and reference. Information handling system may also contain an apparatus for supplying control signals and power to fluid sampling tool 100.

In examples, fluid sampling tool 100 may include one or more enhanced probe sections 704. Each enhanced probe section may include a dual probe section 706 or a focus sampling probe section 708. Both of which may extract fluid from the reservoir and delivers it to a channel 710 that extends from one end of fluid sampling tool 100 to the other. Without limitation, dual probe section 706 includes two probes 712, 714 which may extend from fluid sampling tool 100 and press against the inner wall of wellbore 104 (e.g., referring to FIG. 1). Probe channels 716, 718 may connect probes 712, 714 to channel 710 and allow for continuous fluid flow from the formation 106 to channel 710. A high-volume bidirectional pump 720 may be used to pump fluids from the formation, through probe channels 716, 718 and to channel 710. Alternatively, a low volume pump bi direction piston 722 may be used to remove reservoir fluid from the reservoir and house them for asphaltene measurements, discussed below. Two standoffs or stabilizers 724, 726 hold fluid sampling tool 100 in place as probes 712, 714 press against the wall of wellbore 104. In examples, probes 712, 714 and stabilizers 724, 726 may be retracted when fluid sampling tool 100 may be in motion and probes 712, 714 and stabilizers 724, 726 may be extended to sample the formation fluids at any suitable location in wellbore 104. As illustrated, probes 712, 714 may be replaced, or used in conjunction with, focus sampling probe section 708. Focus sampling probe section 708 may operate and function as discussed above for probes 712, 714 but with a single probe 728. Other probe examples may include, but are not limited to, oval probes, packers, and/or radial or circumferential probes.

In examples, channel 710 may connect other parts and sections of fluid sampling tool 100 to each other. For example, Additionally, formation testing tool 100 may include a second high-volume bidirectional pump 730 for pumping fluid through channel 710 to one or more multi-chamber sections 732, one or more amide side fluid density modules 734, and/or one or more sample side optics analyzers 736.

Figure 8:
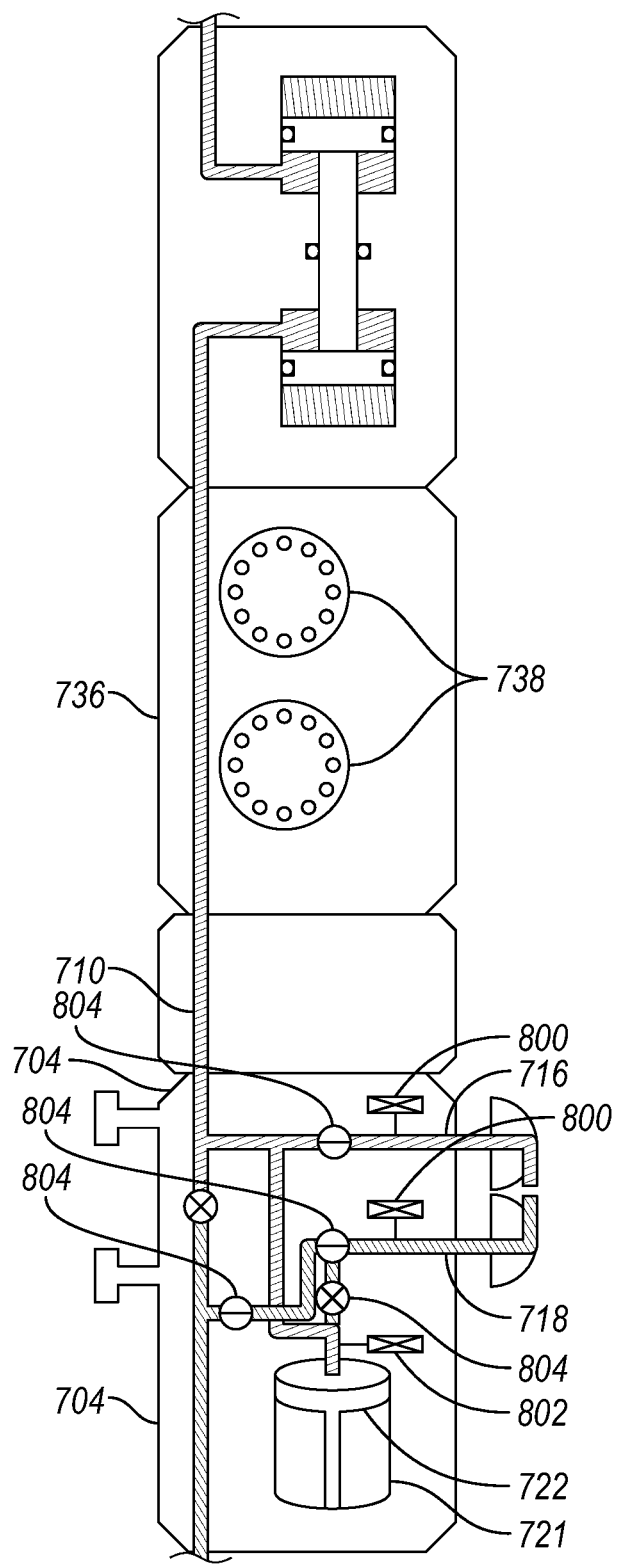
FIG. 8 illustrates an enlarged schematic view of an enhanced probe section.

FIG. 8 illustrates an expanded view of an enhanced probe section 704. As illustrated, enhanced probe section 704 includes low volume pump bi direction piston 722, which is utilized for asphaltene measurements. Asphaltenes are large, high-density hydrocarbons that may be the heaviest component in reservoir fluids. The precipitation and deposition of asphaltenes are a nuisance to any petroleum production system since that may lead to reduction in productivity or injectivity of a well. Asphaltene precipitation and ultimate deposition is caused by a number of factors including changes in pressure, temperature, and composition.

As the reservoir inside formation undergoes primary depletion, the pore (also called reservoir pressure) pressure as well as the flowing bottomhole pressure drops. For a constant temperature, as the decreasing pressure in the reservoir and the wellbore 104 (e.g., referring to FIG. 1) reaches the asphaltene precipitation onset pressure, the dissolved asphaltenes start to precipitate and deposit. This deposition may take place in the reservoir, or near/at the sandface, or in wellbore 104, or in the tubing, or at the surface facilities. This blockage of production paths causes further pressure drops, which results in higher asphaltene precipitation. Over time, this deposition becomes worse until the bubble point pressure is reached. As the pressure falls further below, the asphaltene begins to redissolve into the liquid phase. The deposition of asphaltene may also be caused by changes in fluid composition, and temperature, as well as the introduction of any incompatible chemicals. Identifying when asphaltene falls out of solution is currently performed by laboratory test. To do this, a reservoir fluid sample is taken by fluid sampling tool 170 and extracted at the surface. From there the reservoir fluid sample is sent to a laboratory for analyses.

Analyses of asphaltenes may be performed with any number of scientific evaluations. A few a listed here for reference. One such operation is the Colloidal Instability Index (CII) that was created to illustrate a scale of eventual asphaltene deposition during production. The CII is made up of SARA fractional components and described by the following equation:

$$CII = \frac{\text{Saturates \%} + \text{Asphaltenes \%}}{\text{Aromatics \%} + \text{Resins \%}} \quad (1)$$

The index is governed by the following criteria:
CII≤0.7: asphaltene fraction stable
0.7≤CII≤0.9: asphaltene fraction uncertain
CII≥0.9: asphaltene fraction unstable
The CII may be utilized with methods below to show pressure indicating stability and instability before and after Asphaltene Onset Pressure (AOP).

Another scientific method to analyze asphaltenes is using a refractive index. A Refractive Index (RI) describes the amount of light bending through a medium. RI is proven to accurately describe fluid properties of a hydrocarbon which may be then applied towards reservoir calculations. The refractive index of oil with respect to a Saturates, Aromatics, Resins and Asphaltenes (SARA) fraction by the following equation:

$RI_{oil}$=0.01452×(Saturates %)+0.0014982×(Asphaltenes %)+0.0016624×(Resins %+Asphaltenes %) (2)

At the point of AOP, the RI is described as the Precipitation Refractive Index (PRI). The relation between PRI and $RI_{oil}$ describe a measure that dictates asphaltene stability by the following equation:

Δ(RI)=$RI_{oil}$PRI (3)

The index is governed by the following criteria:
Δ(RI)≤0.045: asphaltene unstable
0.045≤Δ(RI)≤0.060: asphaltene bordering stability
Δ(RI)≥0.060: asphaltene stable To describe the solvency of asphaltenes within an oil mixture, the solubility parameter δ is an important measurement that accounts for molecular forces and energy density of asphaltenes relative to a solution. The Equations below show a relation that describes the solubility parameter of an oil mixture using the oil mixture's refractive index:

$$\delta = 52.042 F_{RI} + 2.904 \quad (4)$$

$$F_{RI} = \frac{(RI^2 - 1)}{(RI^2 + 2)} \quad (5)$$

Where RI is the refractive index of the oil component.

At higher temperatures less amount of asphaltene is precipitated. A corollary effect is that the oil is more soluble and stable for asphaltenes. As such, a parameter defined as the "driving force" is established to dictate the force micro-aggregate asphaltenes have over asphaltenes in solution, which is the difference in solubilities as shown in equation:

Δδ=$\delta_{asph}$−$\delta_{solution}$ (6)

Another scientific model may be used to find the rate of precipitation for asphaltene. It is assumed proportional to the supersaturation degree of asphaltenes that is defined as the difference between the actual concentration of asphaltenes dissolved in oil and the concentration of asphaltene at equilibrium for a specific temperature and pressure. This rate of precipitation may be described mathematically as:

$$\frac{dC}{dt} = k_p(C_A - C_A^{eq}) \quad (7)$$

where $$\frac{dC}{dt}$$

is the rate at which the concentration of asphaltene precipitate changes (i.e., the rate at which dissolved asphaltenes precipitate forming micro-aggregates), $k_p$ is the precipitation kinetic parameter, $C_A$ is the actual dissolved concentration of asphaltenes in solution at given operating conditions, and $C_A^{eq}$ is the concentration of asphaltenes in solution at equilibrium for the given temperature and pressure.

As evidenced from Equation 7 above, the precipitation process is modeled as a first order reaction based on the degree of supersaturation of asphaltenes. The higher the concentration difference between the dissolved and equilibrium concentration, the higher the precipitation rate becomes. This concentration difference or the degree of supersaturation in the context of precipitation starts at 0 which is right at the precipitation onset. With decreasing pressure, the equilibrium concentration at the operating conditions goes down as well and therefore the supersaturation degree increases leading to an increase in the rate of precipitation. Gradually, as the dissolved concentration goes down, the rate of precipitation stabilizes before going down again. Since the dissolved concentration of asphaltenes at every point is not known in the system, the differential equation above can be solved to come up with an expression for the rate of precipitation as:

$$\frac{dC}{dt} = k_p(C_0 - C_A^{eq})e^k p^{\Delta t} \quad (8)$$

where $C_0$ is the concentration of dissolved asphaltenes right before the precipitation onset and $\Delta t$ is the incremental time from that point onwards. Equation 8 may then be used to model the rate of precipitation of asphaltene in a reservoir section once the tuning parameter ($k_p$) is sufficiently known.

Experiments and modeling showed that $k_p$ is lower for higher temperatures as well. Therefore, the following relation was derived to relate the kinetic factor, temperature and driving force:

$$k_p = \exp\left(a_0 \exp\left(\frac{-a_1}{T}\right) - \frac{b_0 \exp\left(\frac{-b_1}{T}\right)}{\Delta \delta}\right) \quad (9)$$

where $a_0$, $b_0$, $a_1$, $b_1$ are constants based on fluid dynamics of asphaltene deposition and T is temperature. From this, the following independent correlations may be observed:

$$k_p \propto \frac{1}{T}, k_p \propto \frac{1}{\Delta \delta}, \text{ and } \Delta \delta_p \propto \frac{1}{T} \quad (10)$$

As discussed below, a gravimetric method may have a similar effect by destabilizing asphaltenes over time with an increased pressure differential $\Delta P'$ from soluble to precipitate. More specifically:

$$\Delta P' = P_{asph} - P_{solution} \quad (11)$$

where $P_{asph}$ are where asphaltene concentrations increase due to precipitation, and $P_{solution}$ is the baseline pressure at which asphaltenes are in solution.

As illustrated in FIG. 8, these laboratory test may be reconstructed downhole using enhanced probe section 704. Specifically, testing methods include the use of housing 721 that includes a low volume bi directional piston 722 within enhanced probe section 704. Housing 721 allows for low volume bi directional piston 722 to draw in fluid for measurement, analyses, or testing within the housing. When sampling operations are being performed, as described above, formation fluid is extracted from a reservoir through a probe, such as focus sampling probe section 708, and into fluid sampling tool 100 through probe channels 716 and 718. As illustrated, probe channels 716 and 718 may each be connected to independent zero offset pressure gauges 800. Fluid sampling tool 100 includes housing 721 and low volume bi directional piston 722, where housing 721 may have 100 cc of capacity and the capability to operate up to 20000 psi below hydrostatic pressure, which is monitored by another high-resolution pressure gauge 802. Additionally, probe channels 716 and 718 have the ability to be isolate from internal flowlines, such as channel 710, from the formation through one or more shut in valves 804 positioned along each probe channels 716 and 718. This allows enhanced probe section 704 to access fluids from either only in fluid sampling tool 100 or reservoir fluid taken through a probe.

During measurement operations, the onset of asphaltenes may be measured utilizing probe section 704 and/or fluid analysis module 736. Within fluid analysis module 736 may be one or more optical measurement tools 738 that are fluidly connected to channel 710. As testing methods are performed with housing 721, additional testing methods may analyze reservoir fluid in channel 710 with one or more optical measurement tools 738 in fluid analysis module 736. Within the fluid analysis module, fluid composition including C1, C2, C3, C4, C5, C6+, Saturates, Aromatics, Resins, and Asphaltene concentrations, Bubble point, viscosity, index of refractions, molecular weight, API gravity, Gas to Oil ratio (GOR), capacitance, dielectric spectroscopy, resistivity, optical throughput may be measured. Changes in these measured properties are many times affected by asphaltene precipitation.

Figure 9:
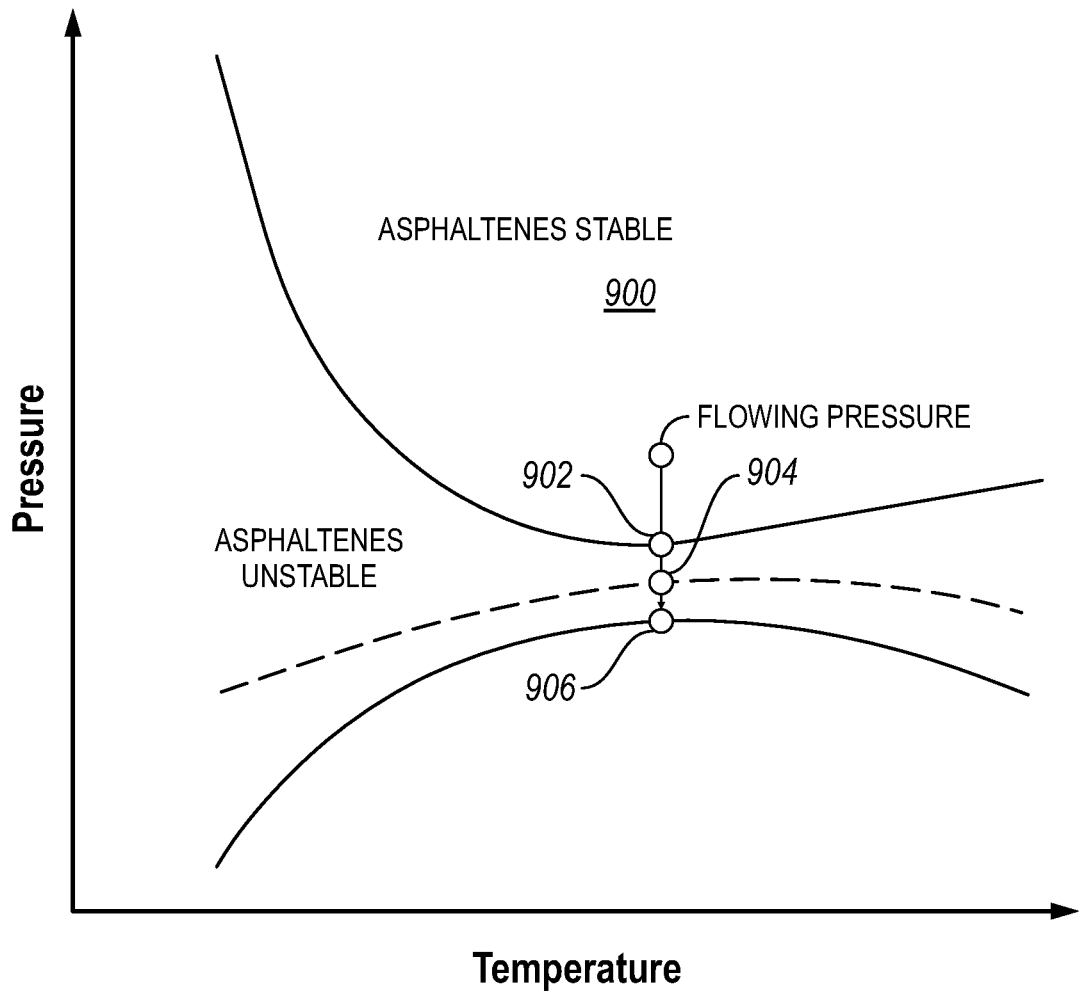
FIG. 9 illustrates a graph illustrating asphaltene phase envelope denoting the stability regions of asphaltenes during production.

FIG. 9 is a graph illustrating asphaltene phase envelope denoting the stability regions of asphaltenes during production. As illustrated, Upper Asphaltene boundary 900 separates asphaltenes in equilibrium denoted "Asphaltene Stable". As a reservoir starts producing (Flowing Pressure) at the sandface, the reservoir eventually depletes and asphaltenes start precipitating at the Upper Asphaltene Onset Pressure (UAOP) 902, where the fluid becomes thermodynamically unstable. As pressure crosses the bubble point (BP) 904, gas evolves from solution and is also near where the peak of asphaltene precipitation exists. The Lower Asphaltene Onset Pressure (LAOP) 906 is the lowest pressure where asphaltenes are out of solution. As the pressure falls further below, the asphaltene begins to redissolve into the liquid and gas phases. This transition is represented with a corresponding increase in asphaltene precipitate from UAOP 902 to the peak at BP 904 and then lowest at the LAOP 906.

Asphaltenes undergo a series of kinetic phases when destabilizing. On Precipitation, asphaltene molecules initially evolve out of solution at the UAOP 902, and they reside as visibly suspended particles. With an increase in precipitation, molecules eventually aggregate and combine in the Flocculation process. If flocculated particles are noticed (or predicted) early enough, they may be easily remediated during production, which will lead to a de-aggregation of flocculated particles is known as Disassociation. However, if flocculation is left without action, they will lead to Deposition. This stage is a considerable threat, where asphaltenes reduce reservoir efficiency by plugging pores in the sandface, depositing on tubing walls. The consequence of not detecting the UAOP 902 early enough may lead to catastrophic consequences and require considerable costly remediation efforts.

Figure 10A:
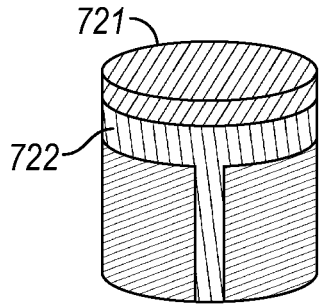
FIG. 10A-10E illustrate stages of measuring asphaltene precipitation.
Figure 10B:
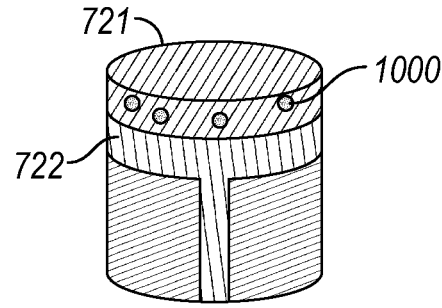

FIGS. 10A-10E illustrate operation of low volume bi directional piston 722 allows for the measurement and analyze of asphaltenes from reservoir fluid to determine UAOP 902, BP 904, and/or LAOP 906 (e.g., referring to FIG. 9). Herein, only a single or multiple measurements of UAOP 902, BP 904, or LAOP 906 at at least two depths may form an AOP map. Referring to FIG. 10A, to begin measurement to analyze asphaltenes at a determined location within wellbore 104 (e.g., referring to FIG. 1), enhanced probe section 704 is activated to allow fluid sampling tool 100 to be in fluid communication with a formation through dual probe section 706 or focus sampling probe 708, as described above. After establishing a formation pressure, an optionally taking samples, a gravimetric test is performed.

Measurements taken by zero offset pressure gauges 800 and high-resolution pressure gauge 802 may be utilized to perform a gravimetric test on an information handling system to determine asphaltene precipitation (e.g., referring to FIG. 8). To perform the gravimetric test, probe channels 716 and 718 (e.g., referring to FIG. 8) may be in fluid communication with the reservoir in the formation. Additionally, it should be noted, that the one or more shut in valves 804 (e.g., referring to FIG. 8) have been activated to isolate low volume bi directional piston 722 and housing 721 (e.g., referring to FIG. 8) from other components and devices in fluid sampling tool 100 (e.g., referring to FIG. 8). Using zero offset pressure gauges 800 and high-resolution pressure gauge 802 (e.g., referring to FIG. 8), flowing pressure, temperature and soluble fluid composition of the oil at a sample point in wellbore 104 are measured. In FIG. 10A, low volume bi directional piston 722 is drawn down at a preprogrammed constant rate, while reservoir fluid is drawn into housing 721 by low volume bi directional piston 722 and is monitored in real time. Herein, the reservoir fluid drawn into housing 721 may be referred to as fluid sample. As such, the fluid sample is at a pressure greater than UAOP and the fluid sample will resemble FIG. 10A with asphaltenes saluted within the fluid sample. As low volume bi directional piston 722 continues depressurization within housing 721, the fluid sample within housing 721 may resemble FIG. 10B, as the pressure of the fluid sample is lowered to UAOP. As illustrated, asphaltene particles 1000 start precipitating at the Upper Asphaltene Onset Pressure (UAOP) point within housing 721. Disposed along channel 710 may be at least one fluid analysis sensor (not illustrated). The at least one fluid analysis sensor may observe an inflection sensitive to Asphaltenes, particles, or mass changes. Fluid analysis sensors may comprise density sensors, compositional sensors, and other standard operating sensors.

The respective pressure and asphaltene concentration are detected by one or more zero offset pressure gauges 800 and/or one or more high-resolution pressure gauges 802. In other embodiments, other components may be measured similar to asphaltene particles 1000, such as, Saturates, Aromatics, Resins, and/or C1-C5%.

Figure 10C:
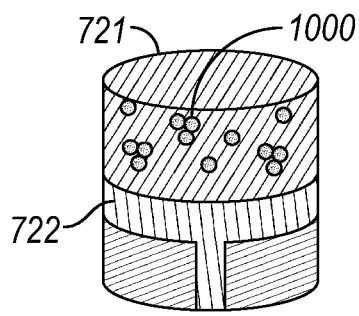
Figure 10D:
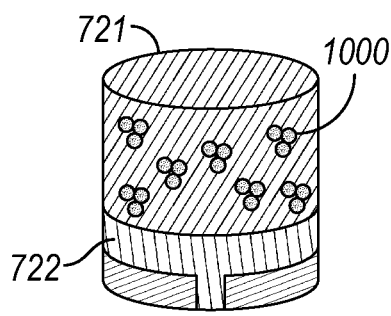
Figure 10E:
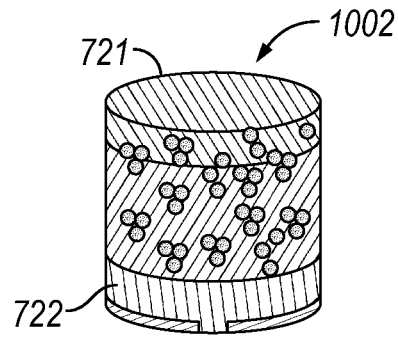

Low volume bi directional piston 722 may further lower the pressure of the fluid sample until it resembles FIG. 10C, in which the fluid sample pressure is equal to the Asphaltene+Resin-Flocculation Onset (ARFO). Evidence of when the fluid sample reaches ARFO may be evident by precipitated asphaltene particles 1000 aggregating and flocculating within the flowline with an inflection in the asphaltene weight percentage. This inflection is detected within housing 721 by fluid analysis sensors as a spike in the first or second derivative. In examples visually or fitting to a knot curve or other suitable curve may identify such an inflection. Subsequently, pressure of the fluid sample may be lowered as previously described until it resembles. In FIG. 4D in which the fluid sample pressure is equal to the bubble point (BP), which is shown in all sensor data that is measuring and analyzing asphaltene particles 1000 within housing 721. In addition, further aggregation to asphaltene particles 1000 occurs as part of flocculation. Finally, pressure of the fluid sample may be lowered as previously described until it resembles FIG. 4E, in which the fluid sample pressure drops below BP. As such, lighter components 1002 liberate from the system and there is a higher concentration of aggregated flocculates of asphaltene particles 1000 in housing 721. At this stage the test is concluded by design and should be considered in the planning process. It is not intended to further depressurize the system to the Lower Asphaltene Onset Pressure (LAOP) point. During this progression, flocculation of asphaltene particles 1000 may transition to deposition, and fluid sampling tool 100 is at risk being plugged and would be inoperable. As a result, no further sampling or pressure tests may be performed, and fluid sampling tool 100 would have to be pulled out to surface. The Gravimetric test may determine the precisely detect the UAOP, ARFO and BP pressures. Additionally, temperature at each pressure is recorded as well. Herein, AOP measurements may be referred to as UAOP, LAOP, ARFO, or BP measurements or any combination thereof.

Following the Gravimetric test, low volume bi directional piston 722 is then moved back to the original position within housing 721, compressing probes 712, 716 back to the reservoir flowing pressure. Subsequently, the shut in valves 804 are opened, via power telemetry section 702, equalizing fluid sampling tool 100, and fluid sampling tool 100 may be retracted and moved to another location within wellbore 104 (e.g., referring to FIG. 1) for further sample or test operations. Additionally, fluid sampling tool 100 may move fluid samples to surface 112. At the surface 112 a series of tests may be conducted to repeat fluid measurements made down hole and to provide a more detailed set of fluid properties including a more detailed composition, and physical properties than mentioned above. Additionally, a full PVT and phase behavior analysis may be performed at surface 112 at a laboratory yielding AOP, UAOP, LAOP, ARFO and BP measurements. Equipment to conduct such analysis include gas chromatographs, liquid chromatographs, mass spectrometers, wet chemistry, PVT cells, viscosimeters, densitometers, and microfluidic systems such as but not limited to PVT microfluidic systems. The above sequences are repeated at every sample point, providing AOP, UAOP, LAOP, ARFO and BP measurements at unique depths and locations within the reservoir independent of the captured fluid sample.

Multiple AOP measurements taken at different positions in a wellbore to form Asphaltene Onset Pressure Map from Asphaltene Onset Pressure Measurements, which are done isothermally. At specific positions within a well the asphaltene onset pressure and or fluid chemical and physical measurements may be made. Additionally, formation measurements may be made. The asphaltene onset pressure map may be formed simply by correlating the AOP measured at various locations to the location or fluid, or rock properties information acquired at the same or similar depths, or modeling may be performed in order to interoperate and extrapolate AOP mapping information. Note that the term mapping may be done digitally as a correlation function or other mathematical function that describes the AOP variation relative to the independent properties such as variations of location. Herein, a location may be defined by vertical depth, lateral distance or extent pressure, temperature, at least one component of reservoir fluid composition, or other state condition. The mapping may take place multidemsionally such that it includes location and geology or compositional information simultaneously and requires a minimum of two distinct AOP measurements. The map result may be a graphical representation, digital representation, mathematical representation, functional representation statistical representation, or other appropriate representation that allows information extraction of the AOP per the mapped properties. An AOP map may be formed as a single dimensional variation with depth, or a two-dimensional (2D) topographical style map with lateral location e.g., north and south. The map may be smooth or jumpy and may also be a contour plot against two dimensions with an AOP, or a color plot on a three-dimensional (3D) surface to demonstrate 3 dimensions with an AOP. The map may also be a multidimensional matrix of data acquired from downhole formation sampling tool, reservoir parameters, geological parameters, and/or petrophysical parameters.

In examples, an equilibrium or disequilibrium composition may be determined within the reservoir. For a continuous reservoir AOP may be smooth as a function of depth or other property that varies smoothly with depth. We will see a discontinuity or abrupt change in first and or second derivative for discontinuities as a function of the independent variable i.e., depth. Same holds for lateral continuity.

In other examples, mechanism for disequilibrium processes may be identified (e.g., Gas migration, gas charging, convection, etc.). This may be performed by modeling the AOP against a property indicative of a process such as gas composition from a gas charge, confirms disequilibrium. Other disequilibrium processes may be water washing, biodegradation faulting, baffling, precipitation, convection. Composition may be a good independent variable to model disequilibrium processes against.

In other examples, identifying behavior of Maltenes (Saturates, Aromatics, Resins) in conjunction with Asphaltenes to quantify chemistry behavior while destabilizing an oil may be performed. For example, identification may be performed by an asphaltene stability index, or phase behavior modeling wherein the phase is the solid asphaltene state. Modified cubic equation of state functions or petrurbed chain statistical associating fluid theory equation of state PC-SAFT EOS have been used, but empirical correlations including machine learning techniques have been used. The composition is an optional input or an optional output for the NN model.

Mapping AOP measurements with isothermal fluid expansion pressure tests may be performed (constant composition expansion) with AOP UAOP, LAOP, ARFO, or BP measurements. Such measurements may be performed by having a fluid analyzer in communication with pressure and rate sensors connected to either a piston or a pump through a flowline or cavity, and a valve that isolates this flowline from the rest of the tool, as discussed above. The section must be in contact directly or indirectly with a pressure measurement and potentially other sensor measurements such as an optical sensor, a compositional sensor, or a density sensor of which are sensitive to the phase of asphaltenes and or concentration of asphaltenes in a specific phase. In the first step, a pump moves reservoir fluid to low contamination values through the formation sampler. Subsequently, a fluid sample is captured not communicated with in the subsequent process. Next a number of valves isolate the flowline connecting the fluid analyzer to the piston (or pump) from the reservoir and rest of the tool. At this point, either the piston or the pump is depressurized at a constant rate selected by the operator. Both the fluid analyzer and pressure sensor measure compositional changes of the fluid with respect to pressure. At a point where asphaltenes are exhibited in the fluid analyzer due to depressurization, the measured pressure is denoted as the Asphaltene Onset Pressure.

Laboratory analysis of recovered fluid samples may be performed. Such Laboratory analysis may comprise finding a laboratory property such as composition by gas chromatography and mass spectrometry and combinations therein, physical properties such as density or viscosity or compressibility, phase behavior analysis, including phase envelops such as but not limited to constant composition expansion, production simulations such as but not limited to differential liberation, fluid compatibility studies, flow assurance studies, slim tube studies for enhanced oil recovery etc. Herein, a laboratory property is defined as at least one measurement in a laboratory, as described above, of at least one fluid sample. Such measurements may comprise compositional properties, physical properties, phase behavior analysis, gravimetric pressure and temperature measurements determined in a laboratory with conventional methods, or any combination thereof. Physical properties are not independent of temperature and pressure but rather directly related. Composition may be related to temperature or pressure if measured as absolute concentration but independent of temperature and pressure if measured as a relative concentration. All physical and chemical properties are interrelated to asphaltene onset pressure. Additionally, multiple fluid samples may be obtained from fluid sampling tool 100. As such, multiple laboratory properties may be measured, as described above from the multiple fluid properties.

A relationship between a laboratory property and an AOP map may be developed using a relational model. The relational model may be based on an equation of state which implements any combination of empirical properties, correlative properties, or stochastic properties. Developing the relation model may comprise forming a correlation between the laboratory property, equation of state, and the AOP map. Forming such a correlation may comprise projecting the laboratory property and the equation of state onto the AOP map. Herein, projecting may be defined as comparing the laboratory property combined with the equation of state to the AOP Map and estimating unmeasured data not previously formed on the AOP map or correcting imperfect data on the AOP map to form a correlation. However, an equation of state is not compulsory to forming a correlation or relational model. The correlation derived from said projection may define the relational model. Additionally, the relational model may update or interpolate the AOP map to locations which were not measured or improve its accuracy, forming an updated AOP map. Improved accuracy of the AOP map may be defined as at least one updated AOP within the updated AOP map, which is closer to the actual AOP from the formation than the measured AOP downhole within the original AOP map.

Figure 6:
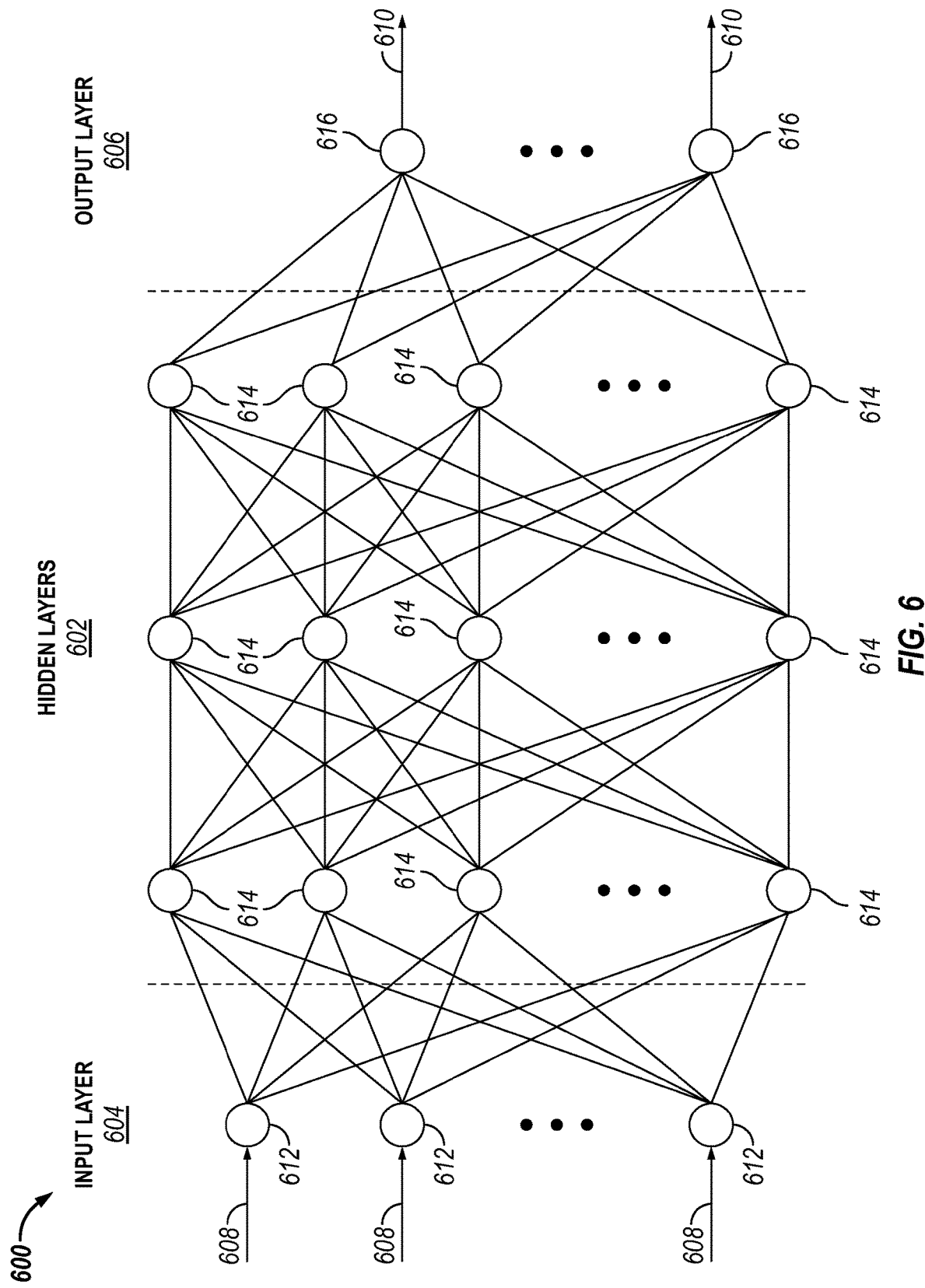
FIG. 6 illustrates a neural network.

In examples, the relational model is thermodynamic such as but not limited to a PC-SAFT equation of state or cubic equation of state. Relational models may also be empirical such and derived through machine learning, as described in FIG. 6. Herein, an update to the AOP map may comprise improving the accuracy of the map with the relationships and correlations developed in the projection. In examples, multiple projections may be derived forming a complex relational model. In further examples, a correlation may also be obtained with a single AOP measured downhole and a laboratory property. Such a correlation may also yield an updated AOP and the updated AOP may be applied to an AOP map, a reservoir simulation, and/or a production analysis.

Methods and systems may perform a reservoir simulation and/or a production analysis with the Relational model and updated AOP map. Generally, the data any AOP map will be digitized, and used to detect when production crosses the threshold of asphaltene precipitation. The fluid properties of the resulting slurry (solid/liquid mixture) may be measured, modeled, assumed, or predicted and used to modify the physical properties of the fluid under various production and or completion scenarios. The scenario modeling will ultimately be used to deploy the physical completion or completion decisions or production analysis from the reservoir simulation. A reservoir simulation may be created from at least the updated AOP map and relational model. Subsequently a production analysis may be developed from the reservoir simulation. As such, if it is desirable to avoid asphaltene precipitation, then the map may be used as a hard boundary for the parameters of the simulation space. Reservoir simulations may be based on finite difference, finite element, analytical modeling, empirical modeling including machine learning analysis techniques and use the relational model derived. Herein, a reservoir simulation may be defined as a prediction or development of the flow of fluids within a formation. In examples a reservoir simulation may comprise the composition of the formation. Additionally, forming the relational model, updating the AOP map, forming a reservoir simulation, and forming a production analysis may implement a NN model as described in FIG. 6.

Similar to production analysis, production decisions may be made with reservoir simulations, but also consider production equipment decisions and remediation techniques. Herein, production decisions may be defined as weather or not to produce a zone, or weather or not to commingle a zone through a production tubing. At what rate to produce a zone. What remediation may be necessary eg asphaltene flocculation or scaling inhibitors. Flow in the casing, combability of fluids and fluid behavior in the surface separation equipment and surface handling equipment are all considered for an economical investment of capital and operational expenses against projected future value of the production fluids. Ultimately the asphaltene onset pressure map with respect to physical location axes (e.g., depth or lateral position), chemical axes and including but not limited to those discussed earlier allow the phase behavior of asphaltenes and chemical response of asphaltenes with respect to changing composition or chemical treatments to be considered in the production and completion designs.

In current technology, asphaltene phase behavior and specifically AOP is not measured downhole to form an AOP map. Instead asphaltene phase behavior is measured in a laboratory usually after production has commenced to determine remediation solutions. Additionally, improvements over current technology reside in projecting laboratory analysis onto an AOP map and updating said map. Further the updated AOP may be used in reservoir simulations or completion and production decisions directly. As such, methods and systems described improve the application of AOP measurements to more than determining remediation solutions.

Statement 1. A method which may comprise disposing a fluid sampling tool into a wellbore, taking a plurality of fluid samples with the fluid sampling tool, identifying a plurality of asphaltene onset pressures (AOP) downhole based at the least on the plurality of fluid samples. The method may further comprise forming an AOP map from at least the plurality of AOPs, identifying a laboratory property from at least one of the plurality of fluid samples; and developing a relational model between at least one of the plurality of AOPs and the laboratory property.

Statement 2. The method of statement 1, wherein the relational model is developed by projecting the laboratory property onto the AOP map.

Statement 3. The method of statement 2, wherein an equation of state is projected with the laboratory property onto the AOP map to develop the relational model.

Statement 4. The method of statement 3, wherein the equation of state are empirical properties, correlative properties, stochastic properties, or any combination thereof.

Statement 5. The method of statements 1 or 2, wherein a laboratory measures the plurality of fluid samples to form the laboratory property.

Statement 6. The method of statements 1, 2, or 5, wherein the laboratory property is compositional properties, physical properties, phase behavior analysis, gravimetric pressure, gravimetric temperature measurement, or any combination thereof.

Statement 7. The method of statements 1, 2, 5, or 6, further comprising updating the AOP map with the relational model to form an updated AOP map.

Statement 8. The method of statement 7, wherein the updated AOP map is interpolated to locations in the wellbore which were not sampled or is closer to the actual AOP from the formation than the measured AOP downhole.

Statement 9. The method of statement 7, further comprising forming a reservoir simulation from the updated AOP map.

Statement 10. The method of statement 9, further comprising performing a production decision from the reservoir simulation.

Statement 11. The method of statements 1, 2, or 5-7, wherein identifying the AOP map comprises performing a gravimetric test.

Statement 12. A system which may comprise a fluid sampling tool with one or more probes for injecting the one or more probes into a wellbore and taking a plurality of fluid samples from the wellbore. The system may further comprise an information handling system to identify a plurality of AOPs downhole from at least the plurality of fluid samples, form an AOP map from the plurality of AOPs, receive a laboratory property from at least one of the plurality of fluid samples, and develop a relational model from at least the AOP map or one AOP from the plurality of AOPs and the laboratory property.

Statement 13. The system of statement 12, wherein the relational model is developed by projecting the laboratory property onto the AOP map.

Statement 14. The system of statement 13, wherein an equation of state is projected with the laboratory property onto the AOP map to develop the relational model.

Statement 15. The system of statement 14, wherein the equation of state are empirical properties, correlative properties, stochastic properties, or any combination thereof.

Statement 16. The system of statements 12 or 13, further comprising a laboratory for measuring the laboratory property from at least one fluid sample from the plurality of fluid samples.

Statement 17. The system of statements 12, 13, or 16, wherein the laboratory property is compositional properties, physical properties, phase behavior analysis, gravimetric pressure, gravimetric temperature measurement, or any combination thereof.

Statement 18. The system of statements 12, 13, 16, or 17, wherein the information handling system updates the AOP map with the relational model to form an updated AOP map.

Statement 19. The system of statement 18, wherein the updated AOP map is interpolated to locations in the wellbore which were not sampled or is closer to the actual AOP from the formation than the measured AOP downhole.

Statement 20. The system of statement 18, wherein the information handling system forms a reservoir simulation from the updated AOP map.

The preceding description provides various embodiments of the systems and methods of use disclosed herein which may contain different method steps and alternative combinations of components. It should be understood that, although individual embodiments may be discussed herein, the present disclosure covers all combinations of the disclosed embodiments, including, without limitation, the different component combinations, method step combinations, and properties of the system. It should be understood that the compositions and methods are described in terms of "including," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present embodiments are well adapted to attain the ends and advantages mentioned as well as those that are inherent therein. The particular embodiments disclosed above are illustrative only, and may be modified and practiced in different but equivalent manners apparent to those skilled in the art having the benefit of the teachings herein. Although individual embodiments are discussed, the disclosure covers all combinations of all of the embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of those embodiments. If there is any conflict in the usages of a word or term in this specification and one or more patent(s) or other documents that may be incorporated herein by reference, the definitions that are consistent with this specification should be adopted.

What is claimed is:

1. A method comprising:
   disposing a fluid sampling and analysis tool into a wellbore;
   measuring asphaltene onset pressures (APO) using the fluid sampling and analysis tool;
   measuring at least one of a reservoir fluid chemical or physical property or a rock property;
   conveying the fluid sampling and analysis tool to at least two different positions in the wellbore and repeating the steps of measuring the asphaltene onset pressure and measuring at least one of the reservoir fluid chemical or physical property or rock property for each of the at least two different positions in the wellbore;
   forming an asphaltene onset pressure man based on the asphaltene onset pressure measurements acquired in the at least two different positions in the wellbore;
   taking a plurality of fluid samples with the fluid sampling and analysis tool;
   measuring at least one laboratory property of the fluid samples in a laboratory;
   combining the asphaltene onset pressure measurements and the at least one of the reservoir fluid chemical or physical property or rock property measurements acquired in the at least two different positions in the wellbore with the at least one laboratory property of the fluid samples measured in the laboratory to develop a relational model comprising a relationship between at least one of the and the asphaltene onset pressure measurement and the at least one laboratory property;
   interpolating at least one asphaltene onset pressure to at least one location where the asphaltene onset pressure was not measured based on the relational model;
   updating the asphaltene onset pressure map with the at least one interpolated asphaltene onset pressure; and
   evaluating production and/or completion scenarios based at least in part on the updated asphaltene onset pressure map.

2. The method of claim 1, wherein the relational model is developed by projecting the laboratory property onto the AOP map.

3. The method of claim 2, wherein an equation of state is projected with the laboratory property onto the AOP map to develop the relational model.

4. The method of claim 3, wherein the equation of state are empirical properties, correlative properties, stochastic properties, or any combination thereof.

5. The method of claim 1, wherein a laboratory measures the plurality of fluid samples to form the laboratory property.

6. The method of claim 1, wherein the laboratory property is compositional properties, physical properties, phase behavior analysis, gravimetric pressure, gravimetric temperature measurement, or any combination thereof.

7. The method of claim 1, further comprising updating the AOP map with the relational model to form an updated AOP map.

8. The method of claim 7, wherein the updated AOP map is interpolated to locations in the wellbore which were not sampled or is closer to the actual AOP from the formation than the measured AOP downhole.

9. The method of claim 7, further comprising forming a reservoir simulation from the updated AOP map.

10. The method of claim 9, further comprising performing a production decision from the reservoir simulation.

11. The method of claim 1, wherein identifying the AOP map comprises performing a gravimetric test.

12. A system comprising:
    a fluid sampling tool with one or more probes, wherein the fluid sampling tool is conveyed into a wellbore to:
    measure asphaltene onset pressures (AOP) at different positions in the wellbore;
    measure at least one of a reservoir fluid chemical or physical property or a rock property;
    take a plurality of fluid samples from the wellbore; and
    an information handling system to:
    form an asphaltene onset pressure (AOP) map based on the asphaltene onset pressure measurement;
    receive a laboratory property from at least one of the plurality of fluid samples;
    develop a relational model comprising a relationship between the asphaltene onset pressure map and the laboratory property;

interpolate at least one asphaltene onset ores sure to at least one location where the asphaltene onset pressure was not measured based on the relational model;

update the asphaltene onset pressure map with the at least one interpolated asphaltene onset pressure; and evaluate production and/or completion scenarios based at least in part on the undated asphaltene onset pressure man.

13. The system of claim 12, wherein the relational model is developed by projecting the laboratory property onto the AOP map.

14. The system of claim 13, wherein an equation of state is projected with the laboratory property onto the AOP map to develop the relational model.

15. The system of claim 14, wherein the equation of state are empirical properties, correlative properties, stochastic properties, or any combination thereof.

16. The system of claim 12, further comprising a laboratory for measuring the laboratory property from at least one fluid sample from the plurality of fluid samples.

17. The system of claim 12, wherein the laboratory property is compositional properties, physical properties, phase behavior analysis, gravimetric pressure, gravimetric temperature measurement, or any combination thereof.

18. The system of claim 12, wherein the information handling system updates the AOP map with the relational model to form an updated AOP map.

19. The system of claim 18, wherein the updated AOP map is interpolated to locations in the wellbore which were not sampled or is closer to the actual AOP from the formation than the measured AOP downhole.

20. The system of claim 18, wherein the information handling system forms a reservoir simulation from the updated AOP map.

* * * * *